(12) United States Patent
Vestri et al.

(10) Patent No.: US 9,737,208 B2
(45) Date of Patent: Aug. 22, 2017

(54) OPTICAL COHERENCE TOMOGRAPHY METHOD AND SYSTEM

(71) Applicant: Costruzioni Strumenti Oftalmici C.S.O. S.r.l., Scandicci (Florence) (IT)

(72) Inventors: Gabriele Vestri, Florence (IT); Claudio De Mauro, Siena (IT); Domenico Alfieri, Lastra a Signa (IT); Silvano Pieri, Sesto Fiorentino (IT); Francesco Versaci, Prato (IT)

(73) Assignee: COSTRUZIONI STRUMENTI OFTALMICI C.S.O. S.R.L., Scandicci (Firenze) (IT)

( * ) Notice: Subject to any disclaimer, the term of this patent is extended or adjusted under 35 U.S.C. 154(b) by 0 days.

(21) Appl. No.: 14/779,754

(22) PCT Filed: Mar. 25, 2014

(86) PCT No.: PCT/IB2014/060132
§ 371 (c)(1),
(2) Date: Sep. 24, 2015

(87) PCT Pub. No.: WO2014/155286
PCT Pub. Date: Oct. 2, 2014

(65) Prior Publication Data
US 2016/0051137 A1    Feb. 25, 2016

(30) Foreign Application Priority Data

Mar. 26, 2013  (IT) ................ FI2013A0067

(51) Int. Cl.
*A61B 3/14*     (2006.01)
*A61B 3/10*     (2006.01)
(Continued)

(52) U.S. Cl.
CPC ............ *A61B 3/102* (2013.01); *A61B 3/0008* (2013.01); *A61B 3/0025* (2013.01); *A61B 3/107* (2013.01); *A61B 3/14* (2013.01)

(58) Field of Classification Search
CPC ....... A61B 3/102; A61B 3/0025; A61B 3/107; A61B 3/14; A61B 3/0008; A61F 9/00808;
(Continued)

(56) References Cited

U.S. PATENT DOCUMENTS 5,975,697 A * 11/1999 Podoleanu ............ A61B 3/102
                                                                    351/206
2010/0198198 A1* 8/2010 Roberts ................ A61B 3/0025
                                                                    606/5
2012/0140173 A1   6/2012 Uhlhorn

FOREIGN PATENT DOCUMENTS

EP        2246659         11/2010

OTHER PUBLICATIONS

R. Yadav, et al., Scanning System Design for Large Scan Depth . . . , Optic Letters, vol. 35, No. 11, pp. 1774-1776, 2010.
(Continued)

*Primary Examiner* — Scott J Sugarman
*Assistant Examiner* — Mustak Choudhury
(74) *Attorney, Agent, or Firm* — Lucas & Mercanti, LLP (57) ABSTRACT

The present invention relates to the field of instruments for imaging internal structures of the human body, and in particular of the eye. More specifically it relates to an optimized method and an optical coherence tomography system thereof.

16 Claims, 8 Drawing Sheets

(51) Int. Cl.
*A61B 3/00* (2006.01)
*A61B 3/107* (2006.01)

(58) Field of Classification Search
CPC .. A61F 9/00821; A61F 9/00838; A61F 9/013; G01N 21/4795; G01B 9/02048
USPC .......... 351/205–221, 246; 359/196; 356/345, 356/346, 349, 357; 606/5
See application file for complete search history.

(56) References Cited

OTHER PUBLICATIONS

International Search Report issued in PCT Application No. PCT/IB2014/060132.

\* cited by examiner

OPTICAL COHERENCE TOMOGRAPHY METHOD AND SYSTEM

CROSS-REFERENCE TO RELATED APPLICATIONS

This application is a 371 of PCT/IB2014/060132, filed Mar. 25, 2014, which claims the benefit of Italian Patent Application No. FI2013A000067, filed Mar. 26, 2013.

FIELD OF THE INVENTION

The present invention relates to the field of instruments for imaging internal structures of the human body, and in particular of the eye. More specifically it relates to an optimized optical coherence tomography method and the related system.

BACKGROUND ART

Optical coherence tomography (OCT), also referred to as phase-variance optical coherence tomography, is one of the most powerful and more widespread biomedical imaging techniques. It has applications in several fields of medicine. The ophthalmologic field has greatly contributed to its development and optimization.

In this technique any information relating to the structure of the sample/organ being observed is derived from the radiation reflected back and/or backscattered from regions showing different optical properties within the sample/organ itself.

The OCT technique allows to create two-dimensional or three-dimensional models having a resolution of one to few μms. Besides allowing a morphological study, OCT may reveal other biological properties of the sample being analysed, such as for example flow rate (by means of the Doppler effect) and birefringence (by means of polarisation changes).

OCT has its bases in low-coherence interferometry. The optical set up of the OCT system is based on a Michelson interferometer and, the OCT system operating mode is determined depending on the type of radiation source and detection technique used. Currently, there are two main schemes used in OCT instruments.

In the so-called Time-Domain OCT (TD-OCT) the reflectivity profile of the sample is obtained by having the radiation coming from the sample optical arm interfere with that coming from the reference optical arm, whose path is modified within a certain time interval. The displacement of the reference arm is the measurement of the distance of the sample member that has caused the reflection.

The Fourier Domain OCT (FD-OCT), on the contrary, records in one step, without the need of a mechanical translation of the members in the reference arm, the spectrum fringes caused by the interference of the radiation coming from the sample arm with that coming from the reference arm, in a broad spectral band. The measurement of the distances of the various sample members is obtained by processing the interferogram signal.

The second technique is much faster than the first one in that it reduces the presence of moving parts and also has benefits in terms of signal-to-noise ratio which result in higher image quality.

In turn, the second FD-OCT technique may be applied according to two main embodiments:
  Spectral Domain OCT (SD-OCT), wherein the spectrum is obtained by using a broadband radiation source and a spectrometer which measures its intensity with a linear sensor (line-scan camera);
  Swept Source OCT (SS-OCT), wherein the spectrum is obtained by an individual radiation detector by making the wavelength emitted by the source vary at very high speeds.

For the sake of clarifying the basic concepts underlying the invention, hereinafter reference will be made to a configuration of the SD-OCT type, but with obvious adjustments the man skilled in the art may readily extend the technique that will be illustrated to the other configurations referred to hereinabove and to known variations thereof.

Figure 1:
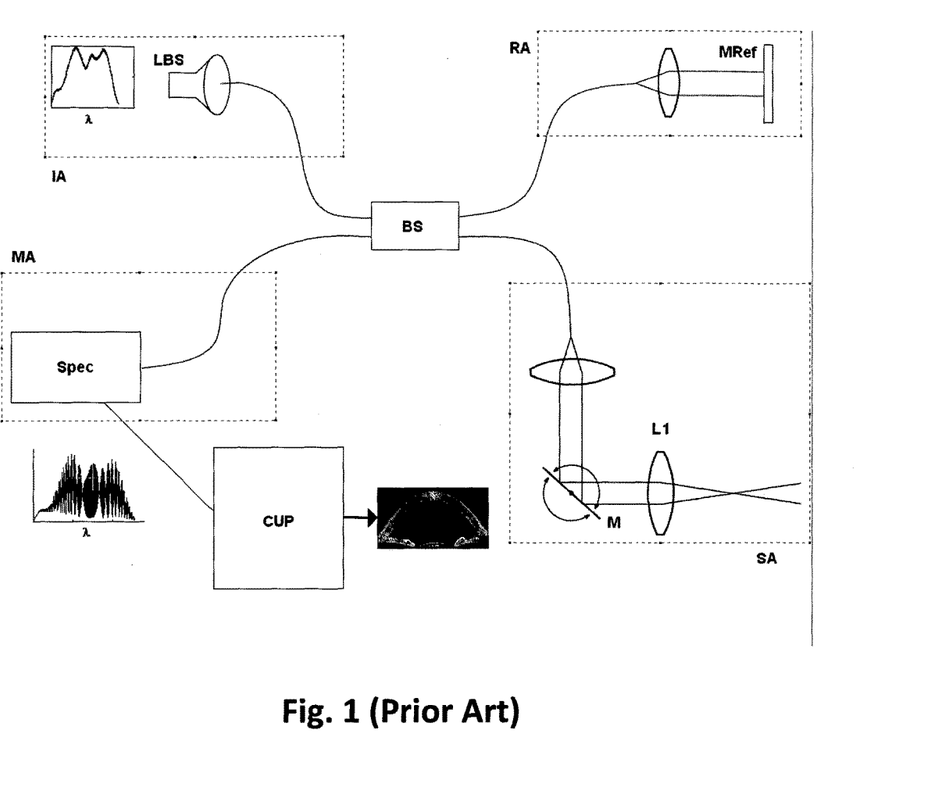
FIG. 1 is a representative scheme of a SD-OCT configuration.

With specific reference now to FIG. 1, which relates to a conventional SD-OCT configuration, the system comprises:
  a broadband radiation source LBS;
  a reference optical arm RA which contains a lens system L2 and a mirror Mref;
  a sample arm SA which contains a scanning system, consisting of a lens system L1 and a mirror and actuator system M, which allows to illuminate a strip (in the axial direction) of the sample of which an image is to be generated and the backscattered radiation is to be collected;
  a signal detection arm MA with a spectrometer Spec which allows to analyse the spectrum of the signal resulting from the interference of the radiation coming from the reference arm RA and from the sample arm SA, comprising a linear sensor detecting the spectrum of the interference signal corresponding to the illuminated strip of the sample;
  a beam-splitter BS configured so that it allows the passage of the radiation from the source LBS to the sample arm SA and to the reference arm RA, and from these to the detection arm MA; and
  a control and processing unit CUP which suitably controls the mechanical and electronic components, and derives from the spectrum, by means of one of the many algorithms known in the literature, a reflectivity profile of the sample strip an image of which is to be generated.

The broadband light radiation source LBS is transmitted to the reference arm RA and to the sample arm SA opposite to which the sample to be imaged is placed. The radiation in the reference arm RA is reflected by the mirror MRef and is sent through the beam-splitter BS to the detection arm MA. Similarly, the radiation in the sample arm SA is backscattered from the illuminated sample portion and arrives through the beam-splitter BS to the detection arm MA. Therefore, the two light waves, coming from the reference arm RA and the sample arm SA, interfere on with the detection arm MA where the spectrometer Spec reconstructs on a linear sensor the spectrum of the interference signal (interferogram).

Figure 2:
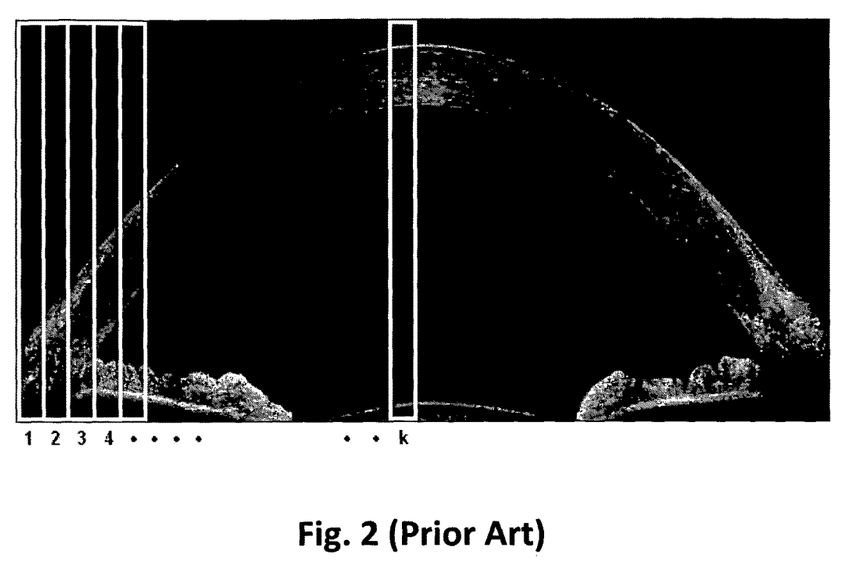
FIG. 2 shows a complete cutaway image of an eye reconstructed by matching individual scan strips with an OCT system.

The above-mentioned spectrum is transformed by means of one of the algorithms known in the literature in the reflectivity profile of the illuminated sample portion. If, for multiple strips, it is possible to measure the reflectivity profile, a cutaway image of the sample may be obtained. From such a cutaway image measurements relating to the sample shape may be obtained. In the case of an eye, for example (see the illustration of FIG. 2), if the eye anterior segment is observed, the altimetrical profile and the curvature of the surfaces of the cornea, the crystalline lens and the iris may be obtained. If many images relating to different sample sections are captured, it may even be possible to generate a three-dimensional model of the sample.

If one decides to use a configuration according to the SS-OCT technique, the an skilled in the art may replace the broadband source with a source having an emitted wavelength that can be varied very quickly over time, and the spectrometer of the detection branch with a single detection channel radiation detector. In this case, the output signal spectrum is built by varying the wavelength emitted by the source and by sequentially storing the intensities measured by the detector for each wavelength.

In order to obtain an image of a section of the eye anterior segment, therefore a linear scan is generally performed and at the end the information obtained is processed into one single image. Then with reference to FIG. 3, if one assumes the use of just one mirror M for a two-dimensional scan, the scan is obtained by changing the inclination of the mirror in the sample arm and consequently the side position of the lighting beam coming from lens O. When the mirror is in position M', the lighting beam R' illuminates the central part of the scanning space and allows the detection of structures in that portion of the sample. When the mirror is in position M", the lighting beam R" illuminates the bottom part of the scanning space. When the mirror is in position M''', the lighting beam R''' illuminates the top part of the scanning space.

Figure 3:
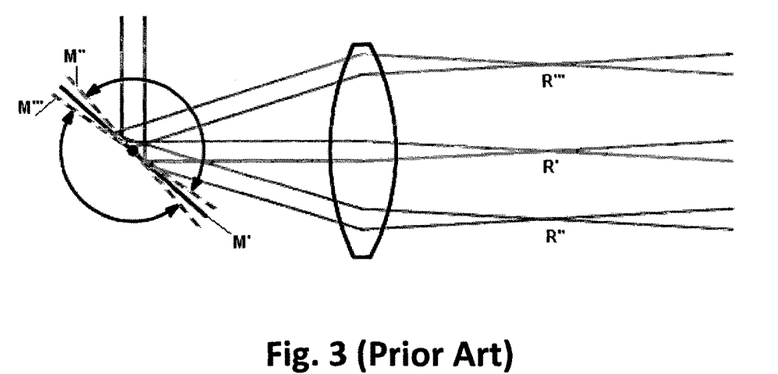
FIG. 3 is a schematic representation of the scan operation on the sample arm of an OCT system.

The illuminated tissue portion backscatters part of the radiation, with an angular scattering of the intensity that depends on its microstructure and the orientation of its discontinuity surfaces. In general such scattering, also referred to as lobe, will be uneven, with an intensity peak in the reflection direction, symmetrical to that of lighting as compared to the normal to said surfaces, and with decreasing intensity in the peripheral directions. The radiation that is actually collected for measurement is that which is backscattered exactly in the opposite direction to that of lighting. Such radiation, which returns to the instrument, will pass through the sample arm of the interferometer and will interfere in the detection arm with the radiation coming from the reference arm on the spectrometer branch.

Figure 4:
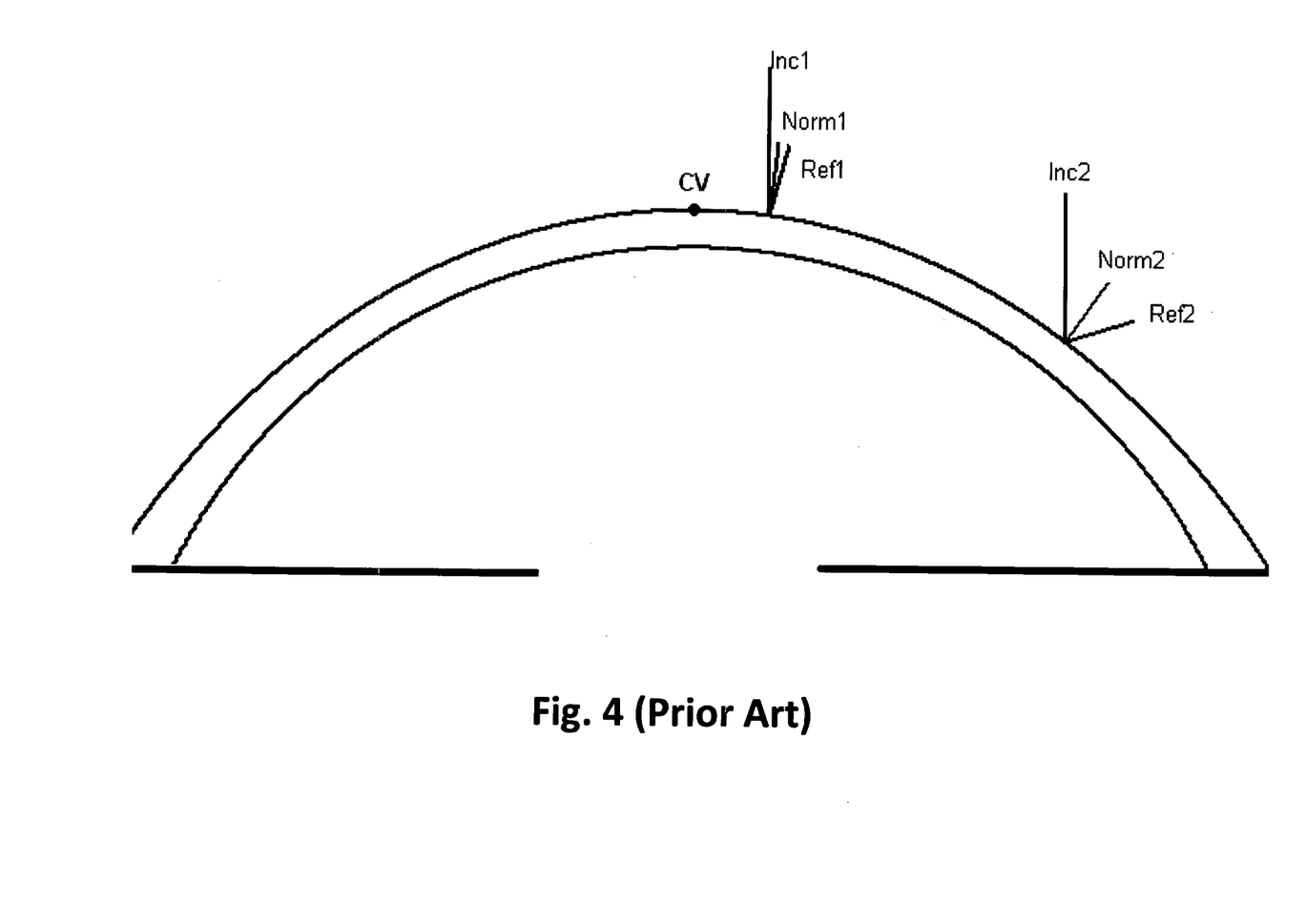
FIG. 4 is a diagram showing the different deviation of scanning beams hitting an eye as a function of the central or peripheral position.

By observing FIG. 4, it may be noted that, if the sample observed has a marked curvature, as in the case of an eye, the more the scan departs from the corneal vertex CV the lower the backscattered power will be in the incidence direction, because a large part of the backscattered energy will be deviated towards the reflection direction, away from that of incidence, and will therefore be lost and unavailable for the detection by the instrument. The above-mentioned figure clearly shows how increasing the incidence angle (angle between the incidence radius Inc1 or Inc2 and the normal to the anterior corneal surface Norm1 or Norm2) also increases the reflection angle and thus the deviation of reflected power (Refl1 or Refl2) towards a direction which is not useful for the instrument to detect a return signal.

A small part of the incident power will however be scattered in the other directions of the lobe, among which is also the one opposing the forward path. In the practice, a reduction in the power collected by the instrument is observed as the scan goes from the centre to the periphery.

In order to address this problem, Rahul Yadav et al. in the paper "Scanning system design for large scan depth anterior segment optical coherence tomography"—OPTICS LETTERS Vol. 35, No. 11/Jun. 1, 2010, suggest a particular configuration of the scanning system consisting of concave mirrors and lenses, which allows the scanning beams to get to the cornea almost as normal or, in other words, with a lower incidence angle. This certainly provides an increase in the quantity of radiation backscattered towards the instrument and results in an increased signal-to-noise ratio.

However, some significant shortcomings are also found. Firstly, the system is complex and expensive because it envisages the use of lenses and mirrors of a non-classical shape and further the various members must be spatially disposed at precise angles, which can make the alignment very demanding and difficult. Further, the system may be very bulky, especially if a quite wide working distance is selected, such that it reduces the discomfort for the patient and/or is needed for the coexistence of other integrated instruments with the one described.

SUMMARY OF THE INVENTION

The applicant has now found a solution that effectively addresses the problem outlined above, without however involving the shortcomings related to the use of complex, expensive and/or hard to configure components, but, on the contrary, by obtaining the result with relatively simple structural and functional interventions and that do not entail any relevant increase in bulkiness, nor do they make uncomfortable the examination for the patient.

According to the invention, an optical coherence tomography system and method has the essential features referred to in the appended claims one and nine.

In brief, given a sample of which an image is to be reconstructed having a surface with a slope variation, for example but not necessarily a marked curvature, the concept underlying the invention is to make the amount of energy of the return signal constant at each scanning position without introducing relevant variations to the classical optical configuration, thus reducing costs, assembly complexity and allowing to use a much higher working distance. To that end, the intensity of the signal collected at the scanning positions corresponding to a high incidence angle is increased. In this way it is possible to obtain an increase in the signal at the peripheral scanning positions, and therefore improve the quality of the image obtained.

In one aspect of the invention, the mirror M is left (again according to the simpler scheme of one single mirror for a two-dimensional scan described above) for a longer time at the positions corresponding to a peripheral scanning step, that is, at positions where the angle formed between the radiation hitting that sample surface and the normal to the surface itself at the hitting point is greater than a scanning step in the central part and, at the same time, allowing the spectrometer sensor to collect the signal in the detection arm MA for a longer time at the positions corresponding to the peripheral scan than the scan in the central part. In this way, the energy received by the sensor from the peripheral areas may be adapted to the amount of backscattered power at the eye strip currently illuminated.

In another (alternative, but also associable to the preceding) aspect of the invention, the intensity of the radiation emitted by the source LBS is varied, in particular by increasing the radiation emitted by the source as the scan moves from the central (corneal vertex area) to the peripheral area.

BRIEF DESCRIPTION OF THE DRAWINGS

The features and the advantages of the optical coherence tomography method and system according to the present invention will be apparent from the following description of an embodiment thereof, reported by way of a non-limiting example, with reference to the annexed drawings, wherein.

DETAILED DESCRIPTION OF THE INVENTION

With reference to said figures, and based on what has already been disclosed in the introductory part with regard to the general architecture of the system, it is assumed, for simplicity of description, that the mirror system of the OCT system according to the invention contains just one mirror M for a two-dimensional scan, but the assumptions below may readily be extended by the man skilled in the art to the case of more than one mirror and for a three-dimensional scan. Naturally, reference is also made to the use of the OCT system for screening and imaging a sample with a marked curvature, mainly in alignment on a human eye.

Figure 5:
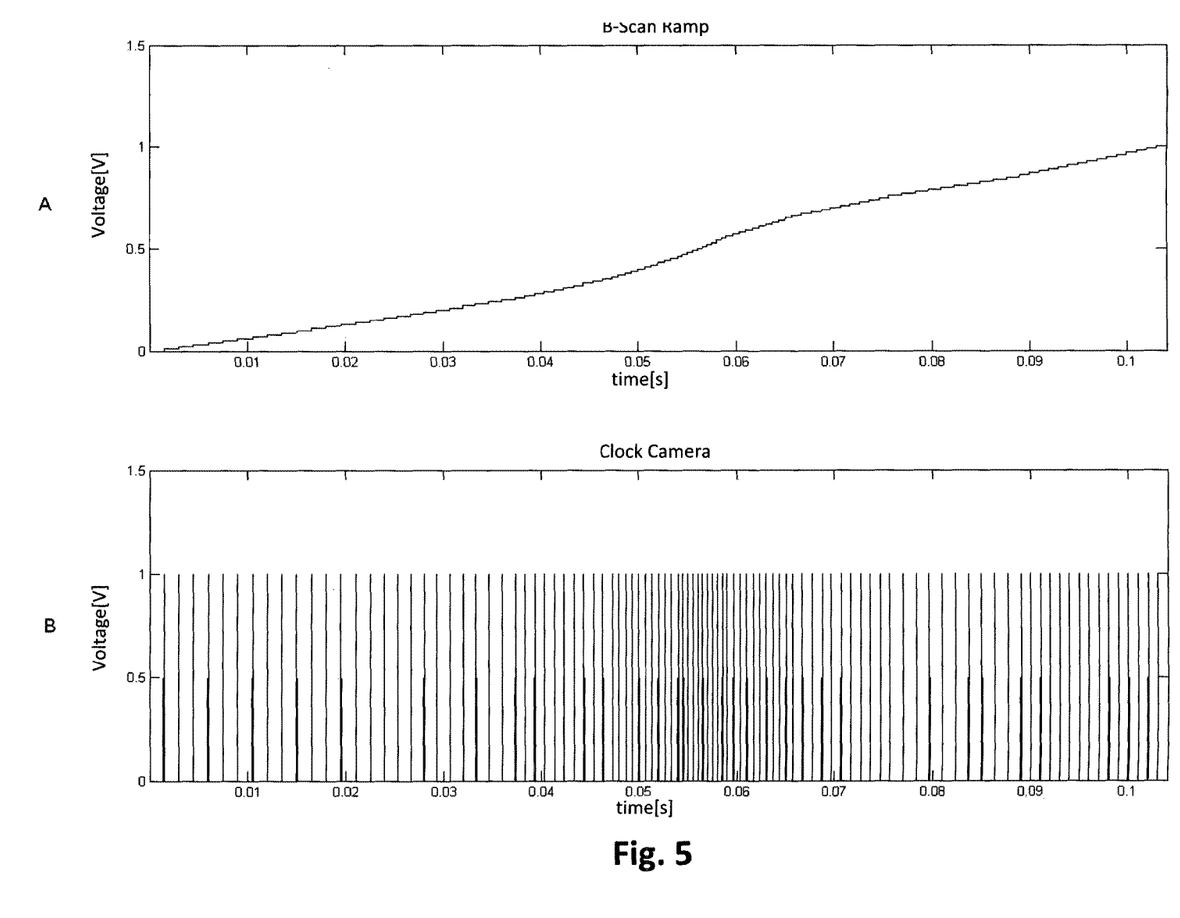
FIG. 5 provides in the form of a diagram an example of a driving ramp for a scanning mirror and a driving timing for the exposure of the sensor according to the invention.

According to one aspect of the invention, in particular with reference to FIG. 5, the movement of mirror M is electronically driven with a control waveform (power supply voltage of the driving motor as a function of time for a cycle that provides for the rotation of the mirror in the direction periphery-centre-periphery of the eye) having such a pattern that allows mirror M to remain for a determined and shorter time interval at the positions corresponding to the scanning step of the central part of the eye, and for a longer time at the positions corresponding to peripheral scans, that is, farther from the corneal vertex. Consequently (and inversely), the law that determines the start and end of the exposure time of the sensor is derived (bottom diagram in the same FIG. 5). The exposure time is, in fact, shorter (thickening of the lines in the timing diagram) for one central scan and longer for a peripheral scan.

Therefore, in general, as the scan departs from the corneal vertex, in both directions, the stop time increases at the position of interest of the scanning beam and therefore of the mirror M, which position determines the location or distance of the scanning strip with respect to the corneal vertex. In this way, the increase in losses of the backscattered signal is compensated for as the scan goes from the central area of the eye to its periphery.

The two possible waveforms for controlling the scanning mirror M and for adjusting the exposure time of the sensor shown in FIG. 5 are exemplary and assume, as mentioned, that the angular position of the mirror may be controlled under voltage and that it is directly proportional to this voltage that continuously over time is applied to the driving motor of mirror M. It is also assumed that the exposure time of the sensor may be regulated by a pulse train where the distance between to consecutive pulses determines the exposure time of the sensor. The man skilled in the art may naturally extend this example to situations in which the system consists of more than one mirror and the commands for the position of the mirrors and the exposure of the sensor are different from those assumed above.

The top diagram of FIG. 5 clearly shows that the ramp slope changes over time: the slope is lower where the mirror must stop for a longer period on an individual scanning strip and higher where the mirror stops for a shorter time. In particular, the slope is reduced when peripheral areas are scanned where the incidence angle is broader and the stop time, and therefore the exposure time of the signal on the sensor, is longer.

The bottom diagram of the same figure shows a pulse train of the sensor timer corresponding to the driving ramp of the mirror of the top diagram. The interval between two pulses is greater where it is necessary to increase the exposure time of the sensor, that is in peripheral areas, wherein the mirror M moves more slowly to compensate for the reduced power of the sample return signal.

The driving waveforms of the mirror M and the exposure timer of the sensor may be determined in advance according to heuristic considerations or may even be estimated optimally thanks to a pre-scan of the sample being observed. The pre-scan may therefore be followed by a temporally precise and optimized scan wherein the movement of the mirror M and exposure of the sensor are adapted to the structure of the sample being examined thanks to an assessment of the pre-scan itself.

A possible implementation of the control ramps of the scanning mirrors and the exposure time of the sensor may be carried out by means of digital generators of variable voltages, suitably programmable so as to construct control signals and curves having any waveform. The digital ramp, generated according to a shape adapted to that end, may then be transformed into an analogue waveform by a digital analogue converter (DAC), if the positioning control of the mirrors is analogue, or directly sent to the same if the control takes place by means of digital waveforms. A generator of variable digital signals generates an output voltage value that is proportional to a binary datum present at its input, belonging to the set of possible binary data corresponding to an output voltage value. By providing the generator with digital waveforms of a writeable memory, wherein the waveform to generate is stored in a digital format, in terms of binary data, the repeated generation of the ramps and therefore of the scans may easily be implemented, without the need of continually re-programming the generator itself.

According to another aspect of the invention, the intensity of the signal collected at the scanning positions where there is a high incidence angle is increased by increasing the intensity of the radiation emitted by the source LBS, a source that may in fact be selected so as to allow an adjustment of intensity (for example a superluminescent diode). This operating mode does not exclude the preceding one and may, on the contrary, integrate it.

Figure 6:
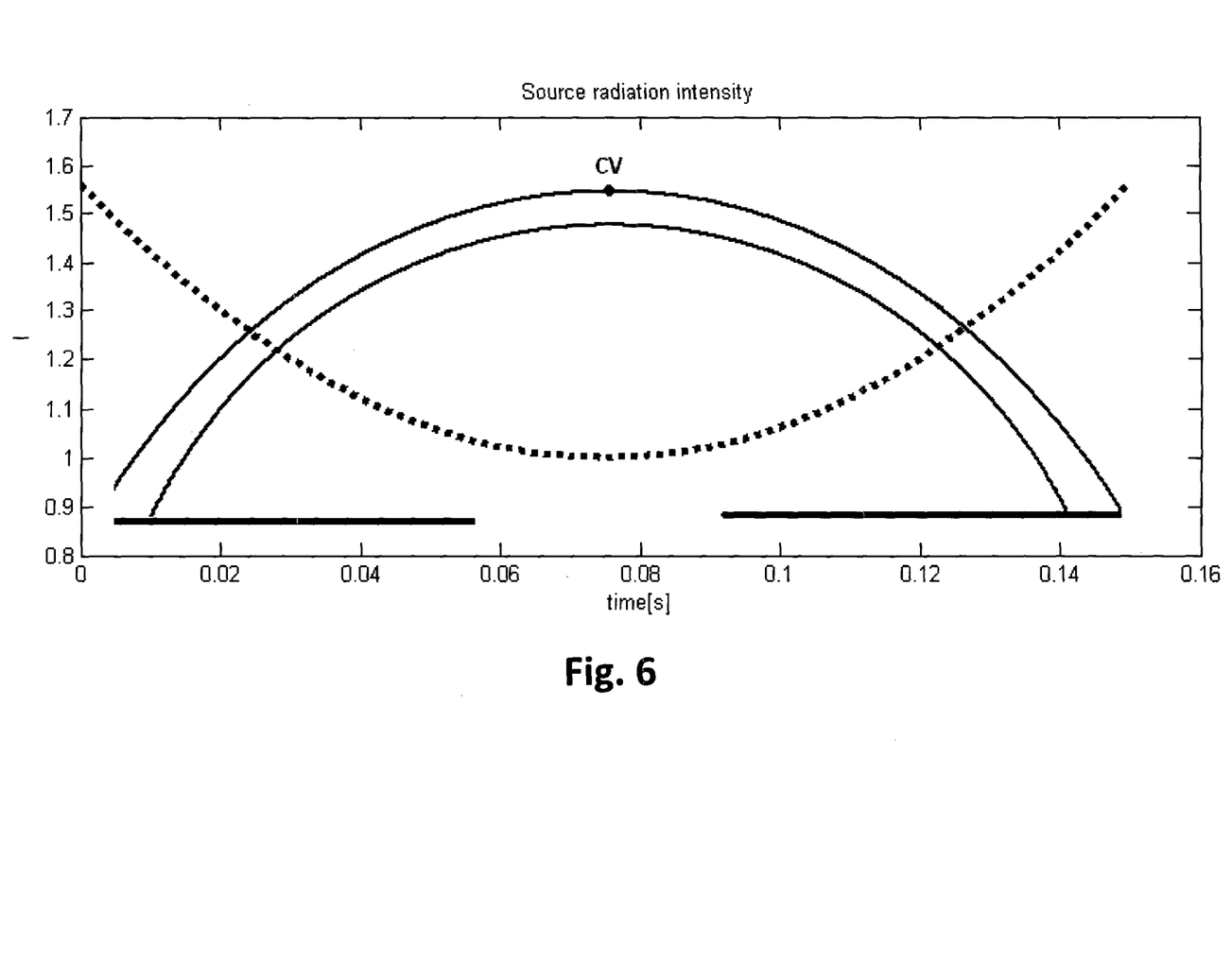
FIG. 6 shows also in the form of a diagram a curve representing a variation in intensity of the light source as a function of time and thus of the position of the scanning mirror with respect to an eye being observed.

The intensity of the radiation hitting the sample, as represented qualitatively in the diagram of FIG. 6, varies gradually so that it is higher at the peripheral scan steps, while it decreases when scanning the central area of the sample, markedly the corneal vertex area where a greater intensity of radiation reflected back and/or backscattered by the eye of which an image is to be generated is available. FIG. 6, in fact, shows an example of a source emission curve based on time variation (time, in turn, corresponds to the passage of the mirror in rotation from a peripheral area to a central area and back to a peripheral area of the eye). The curve pattern and the time scale are merely an indication and must be adapted to the source used and the time required by the particular application.

Even in this case the source emission curve may be determined in advance according to heuristic considerations or estimated thanks to a pre-scan of the sample being observed. The pre-scan method for assessing the laws according to which the variable speed movement of the scanning mirrors, the variation of the exposure time of the sensor and/or the variation in intensity of the source radiation are to be controlled, may be successfully used when the examination time may be sufficiently long, for example when the scan of an individual eye section is needed.

On the contrary, if a high rapidity of the eye examination is required, for example when tens of sections in a few tenths of second are to be captured in order to avoid movements of the eye that may prevent a reliable three-dimensional reconstruction, the determination of the aforementioned laws may be carried out according to different methods allowing to avoid hardly acceptable response delays.

One of such methods envisages the evaluation of the shape of an average eye and thus the determination of the laws on a statistical basis.

A more complex and more precise method is to determine the laws before starting the OCT scan, based on a slope and altimetry measurement of the sample, particularly of the eye, under examination. In order to do so, according to a further embodiment of the invention, one the classical OCT schemes may be coupled with the means needed to assess the shape of the anterior corneal surface. Such means, which constitute per se prior art in the field of ophthalmologic instruments, actually consist of light targets that, when arranged around the optical system L1, are reflected by the cornea or projected by the cornea itself. Their reflected image or projection is collected by a front observation channel of the eye and processed according to algorithms known in the literature.

Figure 7:
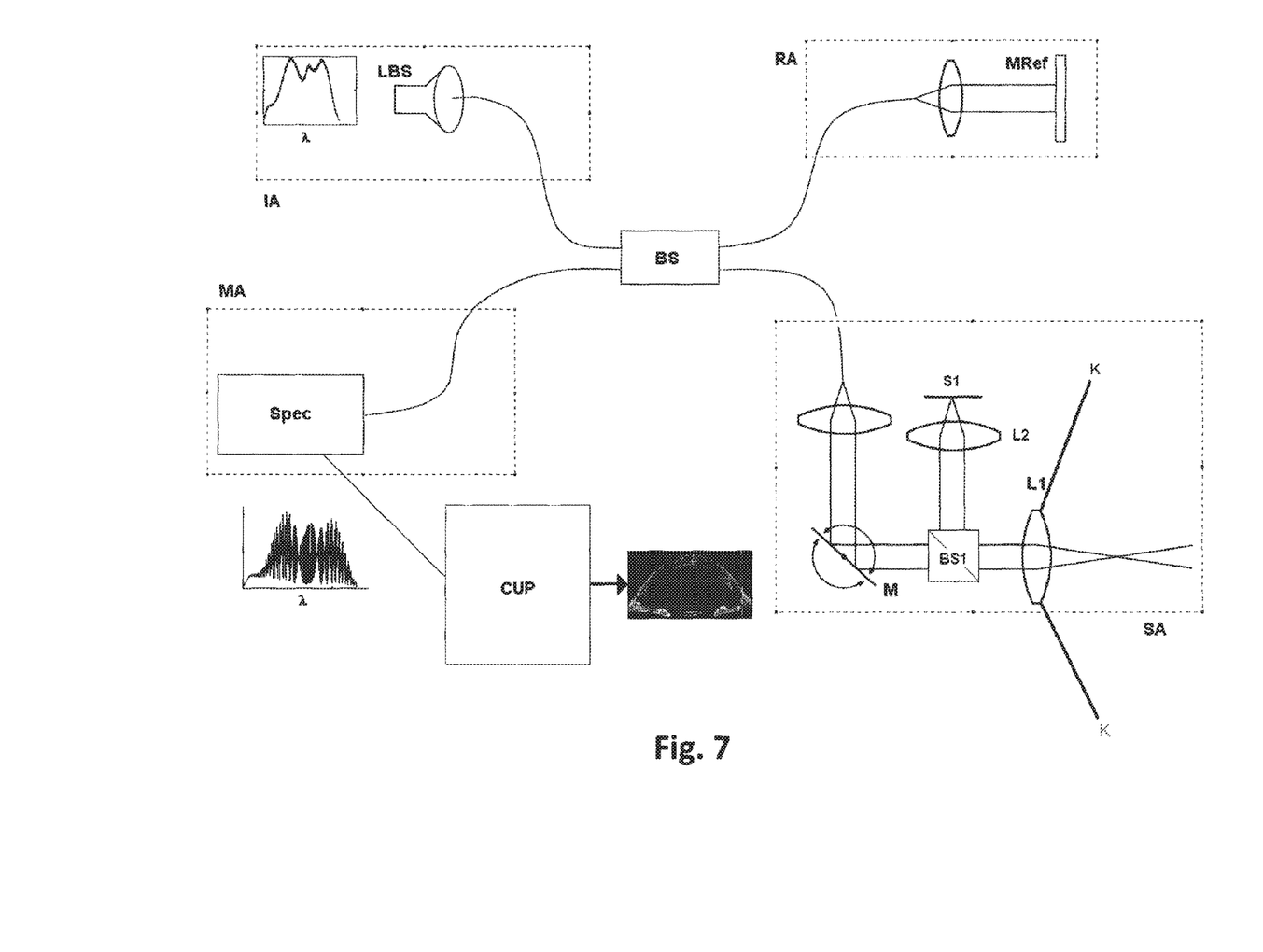
FIG. 7 is a representative scheme of an OCT configuration integrating a keratometer.

In this regard, FIG. 7 shows a possible modification to the architecture of the OCT system according to the invention, integrating the means needed to assess the shape of the front corneal surface, and precisely on the sample arm SA: a keratometer K; the front observation channel comprising lens L1, a beam-splitter BS1, an optical system L2 and a sensor S1.

Figure 8:
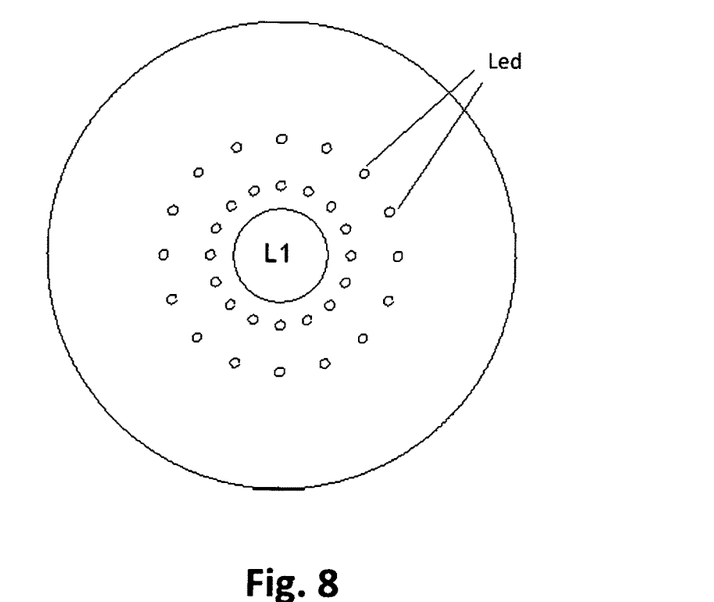
FIG. 8 is a front schematic view of a keratometer of the configuration of FIG. 7 with a double LED crown.
Figure 9:
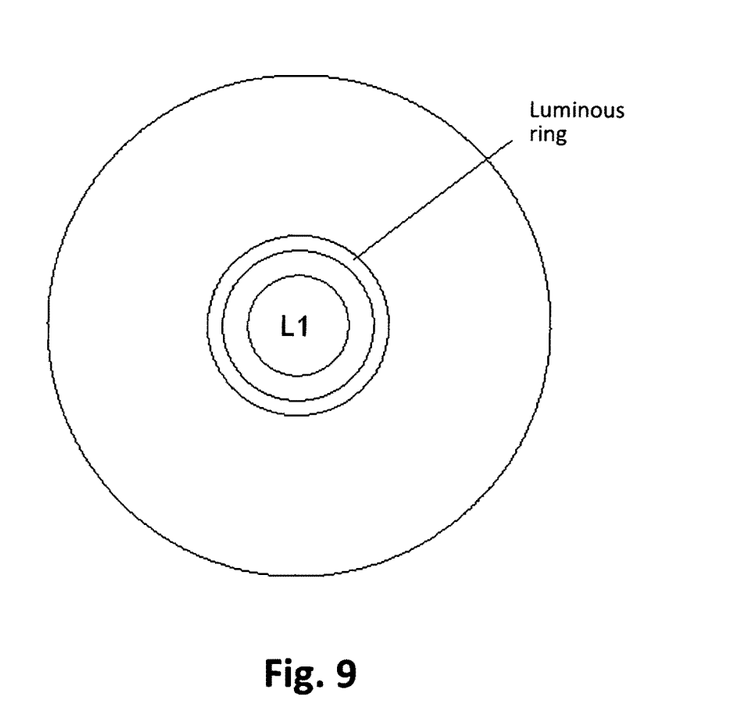
FIG. 9 is a front schematic view of a keratometer of the configuration of FIG. 7 with a luminous ring.
Figure 10:
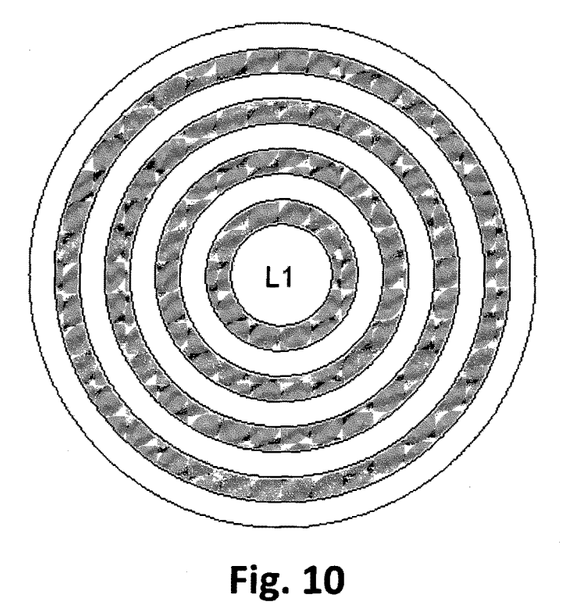
FIG. 10 is a front view of a Placido disk-based topographer, which may be also integrated in the configuration of FIG. 7.

The targets/signs, if one wants to take advantage of reflection, are arranged around the outermost lens L1 of the optical system and may comprise, for example:
 a plurality of light points, for example a double LED crown (FIG. 8);
 a luminous ring (FIG. 9);
 a series of luminous rings or an actual Placido disk (FIG. 10).

For each of the preceding solutions, the algorithms to calculate the shape of the cornea, or its altimetry, slope and curvature from the image of reflected or projected target are known in the literature. If such means are used before the OCT scan it is possible to derive from these, in an optimal way, the local slope of the cornea being examined at each scanning position, and therefore suitably adapt the control laws (of the mirror drive, the sensor exposure, the source radiation intensity).

The keratometer solutions reported above in any case only represent illustrative examples and should not be considered as the only ones adapted to the task. In general, it is possible to use targets having various shapes and sizes from an image the reflection or projection on the cornea of which, collected by the front observation channel, it is possible to derive the morphological information needed by means of algorithms known in the literature.

A further method to estimate the control laws optimized for the eye to be subjected to the OCT scan according to the invention provides for the assessment of the slope of the cornea at the same time as the scan, that is, in other words, by adaptively updating the slope information based on each scanning step previously carried out.

Figure 11:
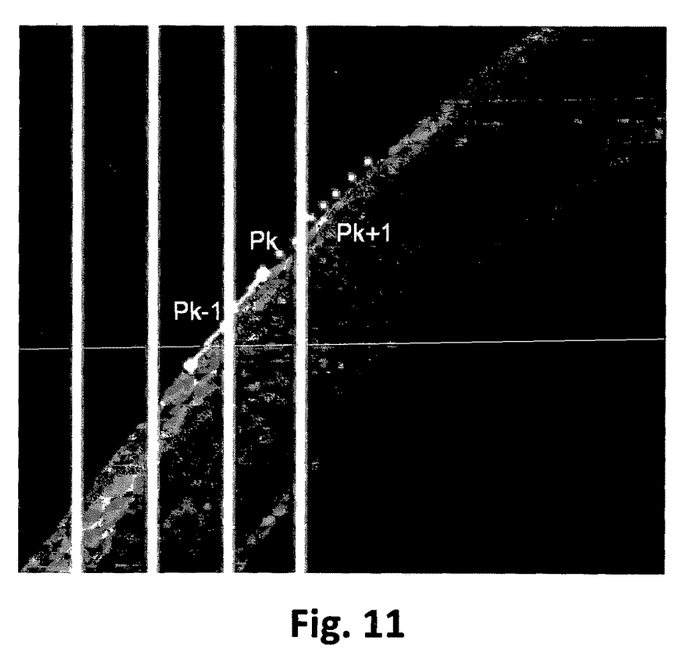
FIG. 11 shows a cutaway image of an eye with a graphical indication of the method of slope linear estimation of cornea that can be used in the system according to the invention.

In greater detail, with reference to FIG. 11, an interferogram of the portion of image captured last (or current capture portion) is transformed in a reflectivity profile thereof, according to notions known or apparent to the man skilled in the art. Also based on techniques known per se, the peaks of the reflectivity profile are identified, by determining the position of the surfaces (in particular of the front corneal surface) hit by the scanning beam at the current scanning position. Such positions are stored. Once the preceding information has been collected for at least two consecutive scans Pk−1 and Pk, it is possible to estimate a local slope of the surface measured. From such slope it is thus possible to derive a reliable prediction to determine a control of the scanning mirrors, the exposure time of the sensor and the intensity of the source radiation, all relating to the following scanning position Pk+1.

If only two preceding scans are considered, it is possible to estimate the aforementioned parameters based on a linear law, as per FIG. 11. Moreover, if more than two preceding scans are considered, the estimate may follow a non linear law, for example a polynomial law of greater magnitude or equal to two.

The present invention has been described thus far with reference to its possible exemplary embodiments. It must be understood that there may exist other embodiments that, in spite of overall optical configurations different from that disclosed herein and integrated by additional components/functionalities, fall within the scope of protection of the appended claims.

The invention claimed is:

1. A optical coherence tomography system comprising: —a broadband light radiation source (LBS); —a reference optical arm (RA); —movable scanning means (M) for scanning a sample, adapted to receive the light radiation emitted by said source to illuminate a portion of the sample corresponding to a position of the scanning means (M), generating a radiation hitting a surface of the same sample, and to collect the backscattered radiation from the sample; a signal detection arm (MA) with at least one sensor adapted to reconstruct the spectrum of the signal resulting from the recombination of the radiation collected by said reference arm (RA) and by said scanning means (M); beam splitter means adapted to permit the passage of the radiation from the source (LBS) to the scanning means and to the reference arm (RA), and from these to the detection arm (MA); and a control and processing unit (CUP) adapted to control the above mechanical and electronic components, to transform said spectrum in a reflectivity profile of the illuminated sample portion, and to generate an image of the sample by juxtaposing a number of profiles each corresponding to a sample portion and obtained further to a displacement of said scanning means; wherein said control means are configured to control an exposure time of said sensor in said detection arm (MA) so that the exposure time, and consequently the intensity of the signal collected by said scanning means (M), progressively increase as scanning positions are taken corresponding to the lighting of sample surface portions in which the angle between radiation that hits said sample surface and a line normal to the same surface at the hitting point is increased.

2. The system according to claim 1, wherein said sample surface is a curved surface, said control means being configured such that the intensity of the signal collected by said scanning means (M) is increased in positions that correspond to the illumination of sample portions in which the direction separation between the hitting radiation and the reflected radiation is increased due to curvature.

3. The system according to claim 2, wherein said scanning means (M) are tiltable about an axis adapted to become aligned with a center of symmetry of said curved surface, said sample portions in which the direction separation between the hitting radiation and the reflected radiation is increased due to curvature being sample portions progressively farther away with respect to said center.

4. The system according to claim 1, wherein said control means are adapted to move said scanning means (M) so that their speed progressively decreases as scanning positions are taken corresponding to the sample portions in which the angle between the radiation that hits said sample surface and the normal to the same surface at the hitting point increases.

5. The system according to claim 1, wherein said control means are adapted to control an exposure time of said sensor in said detection arm (MA) so that the exposure time progressively increases as scanning positions are taken corresponding to the sample portions in which the angle between the radiation that hits said sample surface and the normal to the same surface at the hitting point increases.

6. The system according to claim 1, wherein said control means are adapted to progressively increase the intensity of the radiation emitted by said light source as scanning positions are taken corresponding to the sample portions in which the angle between the radiation that hits said sample surface and the normal to the same surface at the hitting point increases.

7. The system according to claim 1, wherein said control means are configured so that at least said scanning means (M) are controlled based on a preliminary scanning of the sample under examination.

8. The system according to claim 1, comprising or associated with keratometer means adapted to obtain information on the shape of the sample under examination, said control means are configured so that at least said scanning means (M) are controlled based on said information on the shape of the sample obtained by said keratometer means.

9. The system according to claim 1, wherein said control means are configured so that at least said scanning means (M) are controlled by evaluating the angle formed by radiation hitting said sample surface and the normal to the surface at the hitting point based on information adaptively retrieved for each scanning step from a previous step of the same scan.

10. A optical coherence tomography method wherein: —a sample is scanned by collecting a backscattered radiation following a broadband lighting radiation hitting portions of a surface of the same sample; —a sensor reconstructs the spectrum of the signal resulting from the recombination of the radiation collected by an optical reference arm and by the scanning; said spectrum is transformed into a reflectivity profile of the illuminated sample portion, and an image of the sample is generated by juxtaposition of a number of profiles each corresponding to a sample portion and obtained as the scanning advances portion after portion; —wherein in the reconstruction of said signal spectrum the exposure time of said sensor, and consequently the intensity of the signal collected by said scanning, progressively increases as the scanning is carried out in sample surface portions in which the angle between radiation that hits said sample surface and a line normal to the same surface at the hitting point is increased.

11. The method according to claim 10, wherein said sample surface is a curved surface, the intensity of the signal collected by said scanning means (M) being increased in positions that correspond to the illumination of sample portions in which the direction separation between the hitting radiation and the reflected radiation is increased due to curvature.

12. The method according to claim 10, wherein the scanning speed progressively decreases as the scanning is carried out in sample portions in which the angle between the radiation that hits said sample surface and the normal to the same surface at the hitting point increases.

13. The method according to claim 10, wherein the intensity of said illuminating radiation is progressively increased as the scanning is carried out in in sample portions in which the angle between the radiation that hits said sample surface and the normal to the same surface at the hitting point increases.

14. The method according to claim 10, wherein at least the scanning speed is controlled based on a preliminary scanning of the sample under examination.

15. The method according to claim 10, wherein at least the scanning speed is controlled based on information on the shape of the sample obtained by keratometer means.

16. The method according to claim 10, wherein at least the scanning speed is controlled by evaluating the angle formed by radiation hitting said sample surface and the normal to the surface at the hitting point based on information adaptively retrieved for each scanning step from a previous step of the same scan.

* * * * *